United States Patent [19]

Riley et al.

[11] Patent Number: 5,200,547

[45] Date of Patent: Apr. 6, 1993

[54] PREPARATION OF URETHANE AND CARBONATE PRODUCTS

[75] Inventors: Dennis P. Riley, Ballwin; William D. McGhee, St. Louis, both of Mo.

[73] Assignee: Monsanto Company, St. Louis, Mo.

[21] Appl. No.: 576,883

[22] Filed: Sep. 4, 1990

[51] Int. Cl.$^5$ .............................. C07C 68/04
[52] U.S. Cl. ..................... 558/265; 558/260; 558/270; 558/275; 560/24; 560/115; 560/157
[58] Field of Search ............. 560/24, 115, 157; 558/265, 260, 270, 275

[56] References Cited

U.S. PATENT DOCUMENTS

| | | | |
|---|---|---|---|
| 3,655,719 | 4/1972 | Anderson et al. | 558/260 |
| 4,022,813 | 5/1977 | Neri et al. | 558/260 |
| 4,217,298 | 8/1980 | Shikata et al. | 558/260 X |
| 4,467,089 | 8/1984 | Bechara | 544/351 |
| 4,746,716 | 5/1988 | Oates et al. | 558/270 |
| 4,945,179 | 7/1990 | Drent | 560/233 |

FOREIGN PATENT DOCUMENTS

| | | | |
|---|---|---|---|
| 2555629 | 6/1976 | Fed. Rep. of Germany | 558/260 |
| 54-14920 | 2/1979 | Japan | 558/260 |
| 54-16426 | 2/1979 | Japan | 558/260 |

OTHER PUBLICATIONS

Chemistry Express, vol. 1, No. 4, pp. 224–227 (1986) Kinki Chemical Society, Japan.

*Primary Examiner*—Arthur C. Prescott
*Attorney, Agent, or Firm*—Kenneth D. Goetz; Paul L. Passley; James C. Bolding

[57] ABSTRACT

The present invention provides a process for preparing urethanes and carbonates from an amine or an alcohol, carbon dioxide and an allyl halide. The amine or alcohol is reacted with carbon dioxide to form the ammonium carbamate or carbonate salt which is then reacted with a palladium tertiary phosphine catalyst complex of an allyl halide. Polymer products can also be prepared utilizing this process or utilizing the resulting urethanes and carbonates under standard polymerization conditions.

19 Claims, No Drawings

PREPARATION OF URETHANE AND CARBONATE PRODUCTS

BACKGROUND OF THE INVENTION

1. Field of the Invention

The present invention relates to a process for preparing urethanes and carbonates and, more particularly, relates to a new and useful process for preparing urethanes from amines, carbon dioxide and an allyl halide and for preparing carbonates from alcohols, carbon dioxide and an allyl halide.

2. Prior Art

Urethanes and carbonates have been typically synthesized by the reaction of a primary amine or an alcohol with phosgene to form an isocyanate or carbonate. Thereafter, the isocyanate is reacted with an alcohol to form the corresponding urethane. Phosgene is very toxic and thus requires very careful handling from a product and worker safety standpoint. Isocyanates are sensitizers and are extremely toxic as well. Preparing urethane products without using phosgene in an economical manner and without generating isocyanates would be an achievement of considerable significance in the art.

U.S. Pat. No. 4,467,089 discloses the preparation of certain carbamic acid derivatives by the simultaneous reaction of a secondary amine and a tertiary amine with carbon dioxide to produce corresponding tertiary amine salts of N-substituted carbamic acid. The secondary and tertiary amines are brought together in equimolar proportions in the presence of excess carbon dioxide under mild conditions. The secondary amine reacts with $CO_2$ in the presence of the tertiary amine to form the corresponding disubstituted tertiary ammonium carbamate salt. The salt is described as being useful as heat activatable delayed action catalysts, especially for use in polyurethane formulations.

In *Chemistry Express*, Vol. 1, No. 4, pp 224-227 (1986), Kinki Chemical Society, Japan, it is disclosed that primary and secondary amines absorb $CO_2$ to form carbamic acid amine salts and that when an equivalent of 1,8-diazabicyclo[5.4.0]undec-7-ene (DBU) is added, additional $CO_2$ is absorbed to form the DBU-carbamate salt. The DBU-carbamate salt when reacted with an alkylating agent forms a carbamate ester (urethane). Yield and selectivity of the urethane product are highly dependent on the nature of the alkylating agent. When dibutylamine is reacted with $CO_2$ in the presence of DBU and the resulting DBU-carbamate salt is reacted with butyl chloride as the alkylating agent, a yield of only 7% is realized. With butyl bromide, the yield is 86%.

SUMMARY OF THE INVENTION

The present invention provides a new and useful process for making O-allylic urethanes and O-allylic carbonates. A preferred embodiment of the present inventive process is a process for making O-allylic urethanes and carbonates of the following general formula:

wherein $R_1$ represents an allylic radical resulting from the allyl halide moiety; A represents a radical selected from the group consisting of $-NR_2R_3$ and $OR_4$ wherein $R_2$ and $R_3$ independently represent hydrogen and alkyl, alkenyl, cycloalkyl, cycloalkenyl, aryl, aralkyl, alkenaryl and alkaryl radicals having from 1 to about 22 carbon atoms, provided that not more than one of $R_2$ and $R_3$ is hydrogen; and $R_4$ represents alkyl, alkenyl, cycloalkyl, cycloalkenyl, aryl, aralkyl, aralkenyl, alkenaryl, and alkaryl radicals having from 1 to about 22 carbon atoms.

The process for preparing the subject O-allylic urethanes and carbonates is characterized by reacting a suitable primary or secondary mono- or polyamine, or a suitable primary, secondary or tertiary mono-alcohol or polyol, with carbon dioxide to form the corresponding ammonium carbamate salt or carbonate salt which is then reacted with an allyl halide in the presence of a palladium tertiary phosphine catalyst. The reaction is carried out with a strongly basic nitrogenous base, preferably, a tertiary amine base. $R_2$ and $R_3$, together with the nitrogen may be bound to form a saturated or unsaturated heterocyclic 5 to 9 membered ring radical, such as morpholino, pyrrolidino, piperidino, and the like. In addition, one of $R_2$ or $R_3$ can be

wherein R is as defined above for $R_2$, $R_1$ is as defined above and $R_5$ represents alkylene radicals, which may be straight-chain or branched, having from 1 to about 22 carbon atoms, i.e., the new and novel urethanes of this invention may be diurethanes, and $R_4$ can be

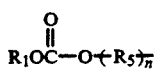

wherein n represents an integer of from 0 to about 8; $R_1$ and $R_2$ are as defined above, and $R_5$ represents alkylene radicals, which may be straight chain or branched, having from 1 to about 22 carbon atoms.

The present invention is based on nucleophilic attack on a $\pi$-allyl palladium tertiary phosphine complex by carbamate anions pre-made from $CO_2$, a primary or secondary mono- or polyamine and a tertiary amine base, or by nucleophilic attack of carbonate anions pre-made from $CO_2$, a primary, secondary or tertiary mono-alcohol or polyol and a tertiary amine base. Urethane products made in accordance with the present invention are useful in specialty chemical applications, such as, for example, as cross-linking agents. Carbonate products made in accordance with this invention are useful in preparing polymers which are useful in shatter-resistant optical lenses, face shields and windows.

DETAILED DESCRIPTION OF THE INVENTION

The urethanes are prepared in accordance with the present invention by bringing into reactive contact a suitable primary or secondary mono- or diamine, or a mixture thereof, carbon dioxide and a tertiary amine base in a confined zone, such as a reactor, to prepare the corresponding ammonium carbamate salt. Similarly, the carbonates are prepared in accordance with the present invention by bringing into reactive contact a suitable primary, secondary or tertiary mono-alcohol or diol, or polyol or a mixture thereof, carbon dioxide and a tertiary amine base in a confined zone, such as a reactor, to prepare the corresponding carbonate salt. Preferably the amines or alcohols are in solution and the carbon dioxide is bubbled through the solution. The reaction proceeds without the need of elevated pressure or temperatures in a slightly exothermic reaction to give either the ammonium salt of the corresponding carbamate anion or the salt of the corresponding carbonate anion. Use of at least an essentially stoichiometric amount of the tertiary amine during the reaction with carbon dioxide provides improved yields of the desired urethane and carbonate products.

A palladium-tertiary phosphine complex which serves as a source of catalytic palladium is prepared and brought into reactive contact with an allyl halide compound in either a solution of the carbamate salt or the carbonate salt, or in a slurry of the ammonium carbamate salt or carbonate salt. The carbamate or carbonate anion attacks the $\alpha$-allyl moiety coordinated to palladium(II) in a nucleophilic fashion. The urethanes and carbonates are then recovered in a conventional manner from the reaction in excellent yields.

The ammonium salt of the carbamate anion can be prepared in solution in the presence of a strong organic base. The use of a strong base shifts the equilibrium toward the production of the carbamate anions. Where the reaction between the primary or secondary amine is carried out in the presence of a base, the reaction may be represented by the equation (1). The resulting ammonium carbamate salt solutions are normally homogeneous.

$$RR'NH + Base + CO_2 = RR'NCO_2^- \ HBase^+ \quad (1)$$

Equation (2) shows the results of the addition of the carbamate anion to an allyl halide in the presence of a palladium catalyst.

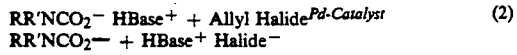

$$RR'NCO_2^- \ HBase^+ + Allyl \ Halide \xrightarrow{Pd\text{-}Catalyst} \quad (2)$$
$$RR'NCO_2 - \ + HBase^+ \ Halide^-$$

Normally, the reaction proceeds smoothly under mild conditions, e.g. at 25° C. and 110 psi carbon dioxide pressure, to give the corresponding O-allylic product in high yields.

Suitable primary or secondary amines used to prepare the carbamate esters in accordance with the present invention can be represented by the following general formula:

$$R_2R_3NH$$

wherein $R_2$ and $R_3$ independently represent hydrogen, provided that no more than one of $R_2$ and $R_3$ is hydrogen, alkyl, alkenyl, cycloalkyl, cycloalkenyl, aryl, aralkyl, caralkenyl, alkenaryl and alkaryl radicals having from 1 to about 22 carbon atoms, which radicals can be straight-chain or branched; and a radical represented by the formula —($-R_5-$)$_n$—NHR wherein R represents radicals as defined above for $R_2$, $R_5$ represents alkylene radicals having from about 1 to about 22 carbon atoms and n represents an integer of from 0 to about 8. Examples of $R_2$ and $R_3$ include methyl, ethyl, n-propyl, isopropyl, n-butyl, isobutyl, t-butyl, n-pentyl, isopentyl, n-hexyl, n-octyl, phenyl, benzyl, and the like. Specific examples of such suitable amines include N-ethyl(benzyl)amine, N,N-diallyamine; N,N-diethylamine; 2-butenyl-1,4-bis(N,N-diethylamine); N-cyclohexylamine; N,N'-dimethylhexamethylene-bis-1,6-diallylamine and the like. In addition, $R_2$ and $R_3$ together with the nitrogen can be bound to form a saturated or unsaturated 5 to 9 membered ring radical. Examples of such ring radicals include morpholino, pyrrolidino, piperidino, and the like. Suitable amines also include polyamines such as, for example, tetraethylene pentamine, diethylene triamine, triethylene tetramine and pentaethylene hexamine.

The amine reacts with $CO_2$ to reversibly form the corresponding ammonium carbamate salt. To shift the equilibrium reaction more favorably to the ammonium carbamate salt, a strongly basic nitrogen-containing base is added. Such nitrogen bases include tertiary amines (e.g., triethylamine, diisopropylethylamine, quinuclidene, etc.), amidines (e.g., DBU, 1,8-diazabicyclo[5.4.0]undec-7-ene, etc.) and guanidines (e.g., tetramethylguanidine, tetraethylguanidine, and the like).

The salt of the carbonate anion can be prepared in solution in the presence of a strong base, such as a strong organic base. The reaction between the alcohol can be represented by the equation (3). The resulting carbonate salt solutions are normally homogeneous.

$$RR'R''COH + Base + CO_2 = RR'R''COCO_2^- \ HBase^+ \quad (3)$$

Equation (4) shows the results of the addition of the complex of equation 3 to a palladium $\pi$-allyl halide complex.

$$RR'R''COCO_2^- \ HBase^+ + Allyl \ Halide \xrightarrow{Pd\text{-}Catalyst} \quad (4)$$

$$RR'R''COCO_2\diagup\diagdown\diagup + HBase^+ \ Halide^-$$

Typically, the reaction proceeds smoothly under mild conditions, e.g., at 25° C. and 110 psi $CO_2$ pressure, to give the corresponding O-allylic product in high yield.

Suitable primary, secondary and tertiary alcohols used to prepare the carbamate esters in accordance with the present invention can be represented by the following general formula:

$$R_7R_8R_9COH$$

wherein $R_7$, $R_8$, and $R_9$ independently represent hydrogen, and alkyl, alkenyl, cycloalkyl, cycloalkenyl, aryl, aralkyl, aralkenyl, alkenaryl and alkaryl radicals having from 1 to about 22 carbon atoms, which radicals can be straight-chain or branched; a radical represented by the formula —($-R_5-$)$_n$—OH wherein $R_5$ and n are as defined above; or when taken together along with C  form an aromatic ring structure. Examples of $R_7$, $R_8$, and $R_9$ include methyl, ethyl, n-propyl, isopropyl, n-butyl, isobutyl, t-butyl, n-pentyl, isopentyl, n-hexyl, n-octyl, phenyl, benzyl, and the like. Specific examples of suitable alcohols include phenol, benzyl alcohol, cyclohexanol, ethanol, n-butanol, isopropanol and the like. Suitable alcohols also include polyols such as, for example, sorbitol, pentaerythritol and the like.

An advantage of the present process is that the reaction between the amine or the alcohol and $CO_2$ proceeds under mild temperature and pressure. Room temperature and a pressure of 110 psi $CO_2$ are suitable. The reaction preferably is carried out between $-78°$ C. and room temperature under a $CO_2$ pressure in the range of 0.1 atmosphere to supercritical pressure.

Allyl halides suitable for use in the present invention can be represented by the formula:

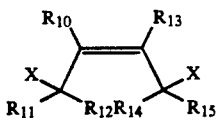

wherein $R_{10}$, $R_{11}$, $R_{12}$, $R_{13}$, $R_{14}$ and $R_{15}$ represent hydrogen and alkyl, alkenyl, cycloalkyl, cycloalkenyl, aryl, aralkyl, aralkenyl, alkaryl and alkenaryl radicals having from 1 to about 22 carbon atoms, which radicals can be straight-chain or branched, and X represents Cl and Br radicals. Examples of radicals encompassed by $R_{10}$ through $R_{15}$ include those radicals exemplified for $R_2$ and $R_3$ and for $R_7$, $R_8$ and $R_9$. Examples of suitable allyl halides include 2-methyl allyl chloride; 1,4-dichloro-cis-2-butene, 1,4-dichloro-trans-2-butene, 4-chloro-2-butene and 3-chlorocyclohexene.

The allyl halide, the palladium (II) catalyst complex, and the ammonium carbamate salts are brought into reactive contact under conditions such that the π-allyl undergoes nucleophilic attack from the carbamate or carbonate anion. The preferred allyl halide is allyl chloride.

The palladium tertiary phosphine catalyst is prepared utilizing a pre-catalyst system, such as, for example, (dibenzylideneacetone)₃Pd₂ (Pd₂dba₃), a tertiary diphosphine such as, for example, 2-bis-diphenylphosphinoethane (DIPHOS), or triphenylphosphine. A preferred tertiary phosphine is DIPHOS. This and other tertiary phosphine catalysts can be prepared by procedures which are well known in the art. For example, utilizing a convenient precatalyst system, e.g., air-stable Pd₂dba₃. To this Pd° system is added a phosphine source, e.g., a tertiary phosphine, in a molar ratio of at least 2 moles of phosphine per mole of palladium. See, for example, Collman et al., "Principles and Applications of Organotransition Metal Chemistry", University Science Books, Mill Valley, Calif., (1987), which is hereby incorporated by reference. Suitable catalysts include Pd₂dba₃+(DIPHOS), Pd(PPh₃)₄; Pd₂dba₃)+(PPh₃); and [Allyl PdCl]₂+PPh₃.

The reaction is carried out in a suitable organic solvent, among which are tetrahydrofuran, DMSO, 1,2-dimethoxyethane, glyme and other ether and polyether solvents, as well as methylene chloride, 1,2-dichloroethane and other chlorinated solvents. Preferred solvents are etherated solvents such as THF and glyme.

To obtain high selectivity of urethanes over amine products (oxygen vs. nitrogen attack) and high selectivity of carbonates over ethers, the anion is stabilized by the use of an essentially stoichiometric amount of a base. The term base as utilized herein refers to a base utilized in addition to the reactant amine or alcohol. This is the tertiary amine base previously defined. Addition of the pre-made carbamate, or carbonate, anion under carbon dioxide pressure to a solution of an allylic chloride with a suitable palladium/phosphine catalyst gives high yields and selectivities of O-allylic urethanes and carbonates and with high rates. The selection of the base in the formation of the carbamate is important in order to obtain higher selectivities and thus higher yields. The base preferably has one of the general structures shown below.

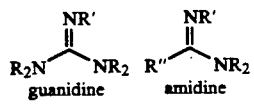

These bases are well known in the art and several are commercially available. Examples of such bases include 1,5-diazabicyclo[4.3.0]non-5-ene (DBN); 1,8-diazabicyclo-[5.4.0]undec-7-ene (DBU); 7-methyl-1,5,7-triazabicyclo[4.4.0]dec-5-ene (MTBD); and cyclohexyl tetramethyl guanidine (CyTMG). Preferably, the molar ratio of base to the amine or alcohol starting materials will be within the range of from about 1:1 to about 10:1. A preferred molar ratio is in the range of from about 1:1 to about 1.5:1. A most preferred molar ratio is 1:1. It is contemplated that mixtures of alcohols and mixtures of amines can be utilized effectively in the process of the present invention. Furthermore, it is contemplated that compounds which include both alcohol and amine functional groups, e.g., diethanolamine, can be utilized effectively in the process of the present invention. In addition, it is contemplated that an alcohol/amine mixture, e.g., a mixture of N-benzyl-N-ethyl amine and benzyl alcohol, can be utilized effectively in the process of the present invention.

Contemplated equivalents of the general formulas set forth above for the alcohols, amines and allyl halides are compounds otherwise corresponding thereto and having the same general properties wherein one or more of the various R groups are simple variations of the substituents as defined therein, e.g., wherein R is a higher alkyl group or includes a substituent such as, for example, a halide, amino substituents, hydroxy substituents and the like. In addition, where a substituent is designated as, or can be, a hydrogen, the exact chemical nature of a substituent which is other than hydrogen at that position is not critical so long as it does not adversely affect the overall synthesis procedure. For example, where the above-specified alcohols and amines are mono- and difunctional alcohols and amines, equivalents thereof which are suitable for use in the present invention include polyols and polyamines.

The chemical reactions described above are generally disclosed in terms of their broadest application to the preparation of the compounds of this invention. Occasionally, the reactions may not be applicable as described to each compound included within the disclosed scope. The compounds for which this occurs will be readily recognize by those skilled in the art. In all such cases, either the reactions can be successfully performed by conventional modifications known to those skilled in the art, e.g., by appropriate protection of interfering groups, by changing to alternative conventional reagents, by routine modification of reaction conditions, and the like, or other reactions disclosed herein or otherwise conventional, will be applicable to the preparation of the corresponding compounds of this invention. In all preparative methods, all starting materials are known or readily preparable from known starting materials.

The invention will now be further disclosed in the following illustrated examples wherein parts and percentages are given on a molar basis unless otherwise specified.

All amines and alcohols used in the following examples were obtained either from Aldrich Chemical Company or Kodak Chemical Company and were used as received. Anhydrous solvents under nitrogen, 1,2-bis(-diphenylphosphino)ethane (DIPHOS), triphenylphosphine, DBN (1,5-diazabicyclo[4.3.0]non-5-ene DBU (1,8-diazabicyclo[5.4.0]undec-7-ene, tris(dibenzylideneacetone)dipalladium $Pd_2dba_3$), tetrakis(triphenylphosphine)palladium, and allylpalladium chloride dimer were purchased from Aldrich Chemical Co.; MTBD (7-methyl-1,5,7-triazabicyclo[4.4.0]dec-5-ene was obtained from Fluka; CyTMG (cyclohexyl tetramethyl guanidine) was synthesized according to the general procedure set forth in Bredereck H.; Bredereck K. Chem Ber. 94, (1961) 2278-2295.

Gas chromatographic analysis was performed on a Varian Model 3400 gas chromatograph with a model 8000 auto sampler using a 30 meter Megabore DB-1 (3 μm) J & W Scientific column. Urethane products were purified and were identified by $^1H$ NMR, $^{13}C$ NMR, mass spectroscopy, IR, and elemental analysis. Nuclear Magnetic Resonance spectra were obtained on Varian VXR-300 or VXR-400 spectrometers. Mass spectra were obtained by FAB or by chemical ionization techniques using isobutane as reagent gas. Infrared spectra were obtained on a Nicolet FT-IR. Molecular weight information of polymer obtained on GPC Waters System comprised of a WISP 700 autosampler, 600E system controller, 500 Å, 10 Å, 10 Å and $10^5$ Å gel permeation columns in series, 410 Differential Refractometer and a Maxima 820 workstation. Molecular weight based on polystyrene standards.

EXAMPLE 1

Into a 6 oz. Fischer-Porter bottle was added 2.708g N-ethyl(benzyl)amine (20.0 mmol), 3.76g DBU (24.7 mmol) and 186 mg tridecane (1 mmol, as internal standard). To this was added 15 mL THF giving a clear solution. The Fischer-Porter bottle was attached to a pressure head and ca. 80 psi carbon dioxide was added above the solution at room temperature with stirring. Upon addition of carbon dioxide the solution warmed slightly and after 2 hours absorption of $CO_2$ had ceased.

Into a second Fischer-Porter bottle was added 99 mg (0.108 mmol) of $dba_3Pd_2$ and 107 mg (0.267 mmol) of bis-diphenylphosphinoethane. This Fischer-Porter bottle was attached to a pressure head. The apparatus was flushed with carbon dioxide followed by the addition of 15 mL THF (dry and air-free) giving a purple solution which slowly turned lighter in color. After 15 minutes 2.89g (50.8 mmol) of allyl chloride was added to the palladium-DIPHOS mixture, the solution turned a dark yellow and was allowed to stir at room temperature for 15 minutes.

The carbamate salt solution was added to the palladium-allyl chloride mixture at room temperature with rapid stirring using carbon dioxide pressure to force the solution from its Fischer-Porter bottle to the reaction vessel. A head pressure of 110 psi of carbon dioxide at 25° C. was added above the reaction mixture. After 2 hours an aliquot was taken from the reaction mixture (during this period of time a large amount of white solid precipitated out of solution). By gas chromatography a yield of 82% of $PhCH_2(Et)NCO_2CHCH=CH_2$ was calculated. The only other product observed by G.C. was ca. 1% of $PhCH_2(Et)NCHCH=CH_2$.

EXAMPLE 2

N-benzyl-N-ethyl allyl carbamate: Into a Fischer-Porter bottle Was added 13.5 g (0.1 mol) N-benzyl-N-ethyl amine, 16 1 g (0.106 mol) DBU and 1 g (5.38 mmol) tridecane (as G.C. internal standard). To this was added 65 mL anhydrous THF giving a clear solution. The Fischer-Porter bottle was attached to a pressure head and ca. 35 psig carbon dioxide was added above the solution at room temperature with stirring. Upon addition of carbon dioxide, the solution warmed slightly and after 2 hours absorption of $CO_2$ had ceased.

Into a second Fischer-Porter bottle was added 100 mg (0.11 mmol) of $Pd_2dba_3$ and 108 mg (0.27 mmol) of DIPHOS (bis-diphenylphosphinoethane). This Fischer-Porter bottle was attached to a pressure head and the apparatus was flushed with carbon dioxide. Anhydrous THF (45 mL) was added to this mixture giving a purple solution which slowly turned yellow. After 15 minutes 16.35 g (0.214 mol) allyl chloride was added and the reaction mixture was allowed to stir at room temperature for 15 minutes.

The carbamate salt solution was added to the palladium-DIPHOS-allyl chloride mixture at room temperature with rapid stirring using excess carbon dioxide pressure to force the carbamate solution into the reactor with the catalyst. A head pressure of 80 psig carbon dioxide was then added above the reaction mixture and the reaction was allowed to stir at room temperature for 21 hours during which time a white solid precipitated. After this time, the pressure was released and the yellow solution was filtered through silica gel (this inactivates the catalyst). The filtrate was concentrated leaving a yellow oil. Distillation at 5 torr (125°–13020 C.) gave 17.17 g (78.4%) of 1 as a clear oil. $^1H$ NMR $(CDCl_3)\delta$ 7.39-7.26 (m, 5H), 6.0 (br, 1H), 5.4–5.2 (br, 2H), 4.69 (br d, J=5 Hz, 2H), 4.54 (s, 2H), 3.32 (br, 2H), 1.13 (br t, J=6.9 Hz, 3H). IR (film) 1705, 1647; MS (CI, methane) m/z=220 (MH+).

EXAMPLE 3

Following the procedure set forth in Example 2 with certain modifications where noted, the following urethanes and carbonates were prepared.

N,N-di-allyl allyl carbamate: Product isolated by distillation at 4 torr (76°–80° C.), 93%. 1H NMR $(CDCl_3)\delta$ 5.93 (m, 1H), 5.78 (m, 2H), 5.26 (dq, J=17.2, 1.7 Hz, 1H), 5.15–5.08 (overlapping m, 5H), 4.54 (dt, J=5.4, 1.5 Hz, 2H), 3.85 (br d, J=5.5 Hz, 4H). $^{13}C\{^1H\}$ NMR $(CDCl_{13})\delta$ 155.9, 135.1, 134.6, 116.7, 116.9, 66.4, 49.6 (br). IR (film) 1705, 1646; MS (CI, methane) m/z=182 (MH+). Anal. Calcd.: C, 66.27; H, 8.34; N, 7.73. Found: C, 66.27; H, 8.01; N, 7.98.

N,N-di-allyl-2-methylallyl carbamate: Product isolated by distillation at 5 torr (78°–85° C.), 67.5%. $^1H$ NMR $(CDCl_3)\delta$ 5.78 (m, 2H), 5.16 (s, 2H), 5.13 (br, 2H), 4.92 (d, J=10.3 Hz, 2H), 4.52 (s, 2H), 3.88 (br, 4H), 1.75 (s, 3H). $^{13}C\{^1H\}$ NMR $(CDCl_3)\delta$ 156.3, 141.1, 134.0, 117.3 (br), 112.5, 69.1, 49.3 (br), 19.9. IR (film) 1705, 1659, 1646; MS (Cl, methane) m/z=196 (MH+). Anal. Calcd.: C, 67.66; H, 8.78; N, 7.17. Found: C, 67.31; H, 8.85; N, 7.11.

N,N-di-ethyl allyl carbamate: Isolated by chromatography on silica gel using 50% $CH_2Cl_2$/hexane (35%): $^1H$ NMR $(CDCl_3)\delta$ 5.97 (m, 1H), 5.32 (dq, J=17.2, 1.7 Hz, 1H), 5.22 (dq, J=10.5, 1.5 Hz, 1H), 4.61 (dt, J=5, 1.4 Hz, 2H), 3.32 (q, J=7.2 Hz, 4H), 1.15 (t, J=7.2 Hz, 6H). —$C\{^1H\}$ NMR $(CDCl_3)\delta$ 156.2, 133.9, 117.3, 66.1, 42 (br), 14.1 (br). IR (film) 1701, 1649.

2-butenyl-1,4-Bis(N,N-di-ethylcarbamate): Product isolated by chromatography on silica gel using 20% ethyl acetate/hexane (22% isolated as clear oil). $^1H$ NMR $(CDCl_3)\delta$ 5.78 (m, 2H), 4.72 (d, J=5 Hz), 3.30 (br q, J=6.9 Hz, 8H), 1.14 (t, J=7.1 Hz, 12 H). —C{$^1$H} NMR (CDCl$_3$)δ 156.2, 128.9, 61.2, 41.9 (br), 14.2 (br). IR (film) 1700; MS (CI, methane) m/z=287 (MH+).

N-cyclohexyl allyl carbamate: Procedure as in Example 2 with following changes: CyTMG used as cobase and reaction carried out at 30° C. Product isolated by chromatography on silica gel using 50% CH$_2$Cl$_2$ 50% hexane (30% isolated as clear oil). $^1$H NMR (CDCl$_3$)δ 5.95 (m, 1H), 5.32 (dq, J=17.2, 1 5 HZ, 1H), 5.23 (dq, J=10.4, 1.4 Hz, 1H), 4.65 (br s, N-H), 4.57 (br d, J=5.4 Hz, 2H), 3.52 (br m, 1H), 1.99–1.10 (m, cyclohexyl, 10H). —C{$^1$H] NMR (CDCl$_3$)6 155.9, 133.6, 118.0, 65.8, 50.4, 33.9, 26.0, 25.3. IR (film) 3325, 1698, 1647; MS (CI, methane) m/z=184 (MH+).

N,N'-dimethylhexamethylene-bis-1,6-(diallylcarbamate): Product isolated by chromatography using 15% ethyl acetate/hexane (50% isolated as clear oil). 1H NMR (CDCl$_3$)δ 5.93 (m, 2H), 5.29 (dq, J=17.2, 1.5 Hz, 2H), 5.19 (dq, 10.4, 1.3 Hz, 2H), 4.57 (dt, J=5.4 Hz, I.4 Hz, 4H), 3.25 (t, J=7.3 Hz, 4H), 2.89 (s, 6H), 1.53 (m, 4H), 1.30 (m, 4H). $^{13}$C{$^1$H} NMR (CDCl$_3$)δ 156.6, 133.8, 117.5, 66.3, 49.2 (br), 36.5 (br) 28.0 (br), 26.9. IR (film) 1700, 1649; MS (CI, methane) m/z=313 (MH+). Anal. Calcd.: C, 61.51; H, 9.03; N, 8.97. Found: C, 61.37; H, 9.01; N, 9.00.

Benzyl allyl carbonate: Procedure as in Example 2 with following changes: CyTMG used as base and reaction carried out at 30° C. Product isolated by chromatography using 100% hexane (64% isolated as clear liquid). $^1$H NMR (CDCl$_3$)δ 7.45–7.30 (m, 5H), 5.98 (m, 1H), 5.40 (dq, 17.2, 1.5 Hz, 1H), 5.30 (dq, J=10.4, 1.3 Hz, 1H), 5.22 (s, 2H), 4.68 (dt, J=5.8, 1.3 Hz, 2H). —C{$^1$H} NMR (CDCl$_3$)δ 155.5, 135.8, 132.1, 129.1, 129.0, 128.8, 119.4, 70.2, 69.1. IR (film) 1754, 1650; MS (FAB, n-BuOH) m/z=181 (MH+).

Phenyl allyl carbonate: Procedure as in Example 2 with following changes: CyTMG used as base and reaction carried out at 30° C. Product isolated by distillation at 20 torr, 85° C. (31% as clear liquid) $^1$H NMR (CDCl$_3$)δ. 7.35 (t,J=7.5Hz, 2H), 7.0. (overlapping,3H), 6.12 (m, 1H) 5.48 (dd,J=17.2, 1.5Hz 1H) 5.35 (dd, J=10.5, 1.4Hz, 1H) 4.60(d,J=5.4Hz, 2H) —C{$^1$H} NMR (CDCl$_3$)δ. 159.2, 133.9, 130.0, 121.4, 118.1, 115.3, 69.3. IR (film) 1746,1650.

While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples and descriptions set forth hereinabove but rather that the claims be construed as encompassing all the features of patentable novelty which reside in the present invention, including all features which would be treated as equivalents thereof by those skilled in the art to which the invention pertains.

EXAMPLE 4

Following the procedure set forth in Example 2, reactions were carried out between N-benzyl-N-ethyl amine, CO$_2$, allyl chloride and a base. The base was varied to demonstrate an increase in selectivity utilizing a guanidine or amidine base as opposed to a tertiary amine, namely, diisopropyl ethyl amine. Results are shown in Table 1.

TABLE 1

| Co-base | % Urethane | % Amine |
|---|---|---|
| (i-Pr)$_2$NEt | 2 | 23 |
| DBN$^a$ | 49 | 13.5 |
| DBU$^b$ | 86.5 | 3 |
| CyTMG$^c$ | 100 | 1 |
| MTBD$^d$ | 104 | <1 |

All reactions run at room temperature under 80–100 psig carbon dioxide in THF using Pd$_2$dba$_3$/phosphine catalyst with tridecane or biphenyl as internal G.C. standard.
$^a$DBN = 1,5-diazabicyclo[4.3.0]non-5-ene.
$^b$DBU = 1,8-diazabicyclo[5.4.0]undec-7-ene.
$^c$CyTMG = cyclohexyl-tetramethylguanidine.
$^d$MTBD = 7-methyl-1,5,7-triazabicyclo[4.4.0]dec-5-ene.

EXAMPLE 5

Reactions were conducted according to the procedure of Example 2 except that various solvents were utilized. As shown in Table 2, the etherated solvents THF and glyme significantly increase selectivity.

TABLE 2

| Solvent | % Urethane | % Amine |
|---|---|---|
| CH$_2$Cl$_2$ | 49 | 34 |
| DMSO | 67 | 3.4 |
| THF | 86.5 | 3 |
| Glyme | 82 | 1 |

All reactions run at room temperature under 80–100 psig carbon dioxide using Pd$_2$dba$_3$/phosphine catalyst with tridecane or biphenyl as internal G.C. standard.
$^a$DBU = 1,8-diazabicyclo[5.4.0]undec-7-ene.

EXAMPLE 6

Reactions were conducted according to Example 2 except that the catalyst was varied. Results are shown in Table 3.

TABLE 3

| Catalyst | % Urethane | % Amine |
|---|---|---|
| [AllylPdCl]$_2$ PPh$_3$ | 85 | 5 |
| Pd$_2$dba$_3$ PPh$_3$ | 88 | 5.5 |
| Pd(PPh$_3$)$_4$ | 90 | 4.5 |
| Pd$_2$dba$_3$ DIPHOS | 98 | 4 |

All reactions run at room temperature under 80–100 psig carbon dioxide in THF with tridecane or biphenyl as internal G.C. standard.
$^b$DBU = 1,8-diazabicyclo[5.4.0]undec-7-ene.

EXAMPLE 7

Various nucleophiles were utilized according to the procedure of Example 2 in combination with various cobases and allyl halides. Results of these reactions are shown in Table 4.

TABLE 4

| Nucleophile | Co-base | Rxn Time | Allylic-Cl | % Urethane or Carbonate | % Amine or Ether |
|---|---|---|---|---|---|
| PhCH$_2$N(Et)CO$_2$ | DBU$^a$ | 2 hr | CH$_2$=CHCH$_2$Cl | 86. | 3 |
| CH$_2$=CHCH$_2$)$_2$NCO$_2$$^-$ | DBU | 2 hr | CH$_2$=CHCH$_2$Cl | 95 | 1.5 |
| CH$_2$=CHCH$_2$)$_2$NCO$_2$$^-$ | DBU | 18 hr | CH$_2$=C(Me)CH$_2$Cl | 87 | <1 |
| Et$_2$NCO$_2$$^-$ | DBU | 2.33 hr | CH$_2$=CHCH$_2$Cl | 91.5 | 1 |
| Et$_2$NCO$_2$$^-$ | DBU | 16 hr | ClCH$_2$CH=CHCH$_2$Cl | 76 | <1 |

TABLE 4-continued

| Nucleophile | Co-base | Rxn Time | Allylic-Cl | % Urethane or Carbonate | % Amine or Ether |
|---|---|---|---|---|---|
| c-$C_6H_{11}$NH$CO_2^-$ | CyTMG[b] | 13 hr | $CH_2$=CHCH$_2$Cl[c] | 101 | <1 |
| $^-O_2$CH(Me)($CH_2$)$_6$N(Me)$CO_2^-$ | DBU | 22 hr | $CH_2$=CHCH$_2$Cl | 66 (diurethane)[d] | 16[d] |
| " | CyTMG | 2¼ hr | $CH_2$=CHCH$_2$Cl | 86[d] | 14[d] |
| PhCH$_2$O$CO_2^-$ | CyTMG | 16 hr | $CH_2$=CHCH$_2$Cl[c] | 88 | ≈1 |
| PhO$CO_2^-$ | CyTMG | 22 hr | $CH_2$=CHCH$_2$Cl[c] | 86 | <1 |

All reactions run under 80-100 psig dioxide pressure in THF at room temperature using Pd$_2$dba$_3$/DIPHOS or PPh$_3$ catalyst with tridecane or biphenyl as internal G.C. standard. All Rxns indicate 100% conversion of carbamate/carbonate.
[a]DBU = 1,8-diazabicyclo[5.4.0]undec-7-ene.
[b]CyTMG = cyclohexyl-tetramethylguanidine.
[c]Reaction run at 30° C.
[d]% amine indicates % allyl-N(Me)(CH$_2$)$_6$N(Me)$CO_2$-allyl.

The products resulting from the above-described process can be utilized to prepare polyurethanes and polycarbonates. Such products can be subjected to any one of many polymerization conditions well known in the art, depending upon the desired end use, e.g., for polyurethanes, in fibers, coatings, moulding applications and the like, and for polycarbonates, in lenses, windows, telephone parts and the like. See, for example, Mark H.; Bikales N.; Overberger C.; Menges G.; Kroschwitz J. "Encyclopedia of Polymer Science and Engineering" 2nd Ed. John Wiley & Sons, New York 1985, which is hereby incorporated by reference. In addition, living polymers can be prepared utilizing diamines, polyamines, diols, polyols or mixtures thereof and diallylic dihalides or poly(allylic)poly(halides).

EXAMPLE 8

Polyurethane from N,N'-dimethylhexamethylene-1,6-diamine and 1,4-dichloro-2-butene.

N,N'-dimethylhexamethylamine-1,6-diamine (7.2 g, 0.05 mole), CyTMG (21.7 g, 0.11 mole) and 30 mL dry THF were added to a Fischer-Porter bottle and attached to a pressure head. To this was added carbon dioxide (60 psig) at room temperature (solution warmed upon addition of $CO_2$).

Into a second Fischer-Porter bottle was added 250 mg Pd(PPh$_3$)$_4$ (0.22 mole), 6.25 g (0.05 mole) 1,4-dichloro-2-butene and 40 ml dry THF.

This was attached to a pressure head and 60 psig $CO_2$ added above the yellow solution. After 1 hr the dicarbamate solution was transferred to the Fischer-Porter bottle containing the Pd complex and allyl chloride. The reaction was allowed to stir at room temperature under 60 psig $CO_2$ pressure for 3 days.

After this time the pressure was released from the reactor and the crude rxn material (yellow solution and white ppt) was filtered through celite using THF to wash the celite. The filtrate was concentrated leaving a brown oil. This oil was dripped into diethyl ether, upon which a thick oily material separated out of solution. This was collected by decanting off the solution and the oil was then washed repeatedly with diethyl ether. GPC analysis gave M=8900, M=5400, $M_w/M_n$=1.66 H[1] NMR (CDCl$_3$)δ 5.75 (br, 2H), 4.71 (d, J=4.4 Hz, 4H), 3.26 (br, 4H), 2.90 (s, 6H), 1.53 (br, 4H), 1.32 (br, 4H). IR (CHCl$_3$) 1692.

What is claimed is:

1. A process for preparing urethanes and carbonates comprising:
    a) bringing $CO_2$ and a primary or secondary amine, an alcohol, an aminoalcohol, or a mixture thereof into reactive contact in the presence of a tertiary amine base, and in a solvent to form the corresponding ammonium carbamate salt or carbonate salt, and
    b) reacting said salt with an allyl halide in the presence of a palladium tertiary phosphine catalyst system.

2. The process of claim 1 wherein said solvent is selected from the group consisting of THF, DMSO,1,2-dimethoxyethane, and glyme.

3. The process of claim 1 wherein the solvent is an etherated solvent.

4. The process of claim 1 wherein the solvent is selected from the group consisting of THF and glyme.

5. The process of claim 1 wherein the palladium tertiary phosphine catalyst system is selected from the group consisting of tris(dibenzylideneacetone)dipalladium+2-bis (diphenylphosphino)ethane, tetrakis (triphenylphosphine)palladium+tris(dibenzylideneacetone)dipalladium; and +triphenylphosphine+triphenylphosphine.

6. The process of claim 1 wherein said tertiary amine base is selected from the group consisting of amidines and guanidines.

7. The process of claim 1 wherein said tertiary amine base is selected from the group consisting of DBU, DBN, MTBD and CyTMG.

8. A process of preparing a compound of the formula:

wherein $R_1$ represents an allyl radical; A represents a radical selected from the group consisting of —NR$_2$R$_3$ and —OR$_4$ wherein $R_2$, $R_3$ and $R_4$ independently represent hydrogen, alkyl, alkenyl, cycloalkyl, cycloalkenyl, aryl, aralkyl or aralkenyl radicals having from 1 to about 22 carbon atoms; or $R_2$ and $R_3$ together with the nitrogen of the radical —NR$_2$R$_3$ may be bound to form a heterocyclic 5 to 9 membered ring radical; or $R_2$ or $R_3$ represents a radical of the formula

or $R_4$ represents a radical of the formula

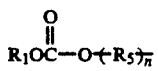

wherein R represents hydrogen, alkyl, alkenyl, cycloalkyl, cycloalkenyl, aryl, aralkyl or aralkenyl radicals having from 1 to about 22 carbon atoms; $R_5$ represents an alkylene radical having from 1 to about 22 carbon atoms and n represents an integer of from 0 to about 8; comprising:

a) bringing $CO_2$ and a primary or secondary amine, an alcohol, an aminoalcohol, or a mixture thereof into reactive contact in the presence of a tertiary amine base, and in a solvent to form the corresponding ammonium carbamate salt or carbonate salt, and b) reacting said salt with an allyl halide in the presence of a palladium tertiary phosphine catalyst system.

9. The process of claim 8 wherein said compound is a urethane of the formula:

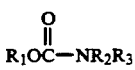

wherein $R_1$ represents an allyl radical; $R_2$ and $R_3$ independently represent hydrogen and alkyl, alkenyl, cycloalkyl, cycloalkenyl, aryl, aralkyl and aralkenyl radicals having from 1 to about 22 carbon atoms; or wherein one of $R_2$ and $R_3$ represent a radical of the formula

wherein $R_1$ is as defined above, R represents hydrogen, alkyl, alkenyl, cycloalkyl, cycloalkenyl, aryl, aralkyl or aralkenyl radicals having from 1 to about 22 carbon atoms, $R_5$ represents alkylene radicals having from 1 to about 22 carbon atoms and n represents an integer of from 0 to about 8; or wherein $R_2$ and $R_3$ together with the nitrogen are bound to form a saturated or unsaturated heterocyclic 5 to 9 membered ring radical.

10. The process of claim 8 wherein said compound is a carbonate of the formula

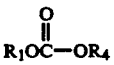

wherein $R_1$ represents an allyl radical and $R_4$ represents alkyl, alkenyl, cycloalkyl, cycloalkenyl, aryl, aralkyl or aralkenyl radicals having from 1 to about 22 carbon atoms and radicals represented by the formula

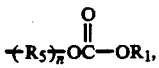

wherein $R_1$ represents radicals as defined above, $R_5$ represents alkylene radicals having from 1 to about 22 carbon atoms, and n represents an integer of from 0 to 8.

11. The process of claim 8 wherein said solvent is selected from the group consisting of THF, DMSO, 1,2-dimethoxyethane, and glyme.

12. The process of claim 8 wherein the solvent is an etherated solvent.

13. The process of claim 8 wherein the solvent is selected from the group consisting of THF and glyme.

14. The process of claim 8 wherein the palladium tertiary phosphine catalyst system is selected from the group consisting of tetrakis (triphenylphosphine)palladium + 2-bis (diphenylphosphino)ethane, tetrakis (triphenylphosphine)palladium; tris(dibenzylideneacetone)dipalladium + triphenylphosphine; and triphenylphosphine.

15. The process of claim 8 wherein said tertiary amine base is selected from the group consisting of amidines and guanidines.

16. The process of claim 8 wherein said tertiary amine base is selected from the group consisting of DBU, DBN, MTBD and CyTMG.

17. The process of claim 8 wherein when R, $R_2$, $R_3$ or $R_4$ is an aryl radical, said aryl radical is selected from the group consisting of alkenaryl and alkaryl radicals.

18. The process of claim 9 wherein when R, $R_2$ or $R_3$ is an aryl radical, said aryl radical is selected from the group consisting of alkenaryl and alkaryl radicals.

19. The process of claim 10 wherein when $R_4$ is an aryl radial, said aryl radial is selected from the group consisting of alkenaryl and alkaryl radicals.

* * * * *